(12) United States Patent
Wyatt

(10) Patent No.: US 7,619,122 B2
(45) Date of Patent: *Nov. 17, 2009

(54) PROCESS FOR PREPARING CYCLOHEXANONE AND CYCLOHEXANOL

(75) Inventor: Larry Walker Wyatt, Augusta, GA (US)

(73) Assignee: DSM IP Assets B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 11/795,563

(22) PCT Filed: Jan. 17, 2006

(86) PCT No.: PCT/EP2006/000521

§ 371 (c)(1),
(2), (4) Date: Apr. 3, 2008

(87) PCT Pub. No.: WO2006/079485

PCT Pub. Date: Aug. 3, 2006

(65) Prior Publication Data

US 2009/0054692 A1 Feb. 26, 2009

(30) Foreign Application Priority Data

Jan. 25, 2005 (EP) .................. 05075184
Jan. 25, 2005 (EP) .................. 05075185

(51) Int. Cl.
*C07C 45/51* (2006.01)
*C07C 35/08* (2006.01)
(52) U.S. Cl. ....................... 568/342; 568/831
(58) Field of Classification Search ............. 568/342
See application file for complete search history.

(56) References Cited

U.S. PATENT DOCUMENTS 4,238,415 A * 12/1980 Bryan .................. 568/342

FOREIGN PATENT DOCUMENTS

| EP | 0 004 105 A1 | 9/1979 |
| EP | 0 659 726 A1 | 6/1995 |

OTHER PUBLICATIONS

International Search Report mailed Apr. 21, 2006 in PCT/EP2006/000521.
Written Opinion mailed Apr. 21, 2006 in PCT/EP2006/000521.

* cited by examiner

*Primary Examiner*—Sikarl A Witherspoon
(74) *Attorney, Agent, or Firm*—Nixon & Vanderhye P.C.

(57) ABSTRACT

Process for preparing cyclohexanone and cyclohexanol, said process comprising (a) neutralising acids and/or carbon dioxide present in an organic solution further comprising cyclohexylhydroperoxide by mixing the organic solution with a first aqueous base solution to form a first mixture comprising a first aqueous phase and a first organic phase, (b) separating first aqueous phase from first organic phase, (c) discharging first aqueous phase, (d) decomposing cyclohexylhydroperoxide present in said first organic phase by mixing said first organic phase with a second aqueous base solution to form a second mixture comprising a second aqueous phase and a second organic phase comprising cyclohexanone and cyclohexanol, (e) separating the second aqueous phase from the second organic phase, (f) feeding at least a portion of said separated second aqueous phase to said neutralising (a), wherein the process further comprises feeding such a portion of the first aqueous phase to the decomposing that the pH of the first aqueous phase is higher then 8.5, measured at 25° C.

13 Claims, 1 Drawing Sheet

PROCESS FOR PREPARING CYCLOHEXANONE AND CYCLOHEXANOL

The present invention provides a process for preparing cyclohexanone and cyclohexanol, said process comprising
(a) neutralising acids and/or carbon dioxide present in an organic solution further comprising cyclohexylhydroperoxide by mixing the organic solution with a first aqueous base solution to form a first mixture comprising a first aqueous phase and a first organic phase,
(b) separating first aqueous phase from first organic phase,
(c) discharging first aqueous phase,
(d) decomposing cyclohexylhydroperoxide present in said first organic phase by mixing said first organic phase with a second aqueous base solution to form a second mixture comprising a second aqueous phase and a second organic phase comprising cyclohexanone and cyclohexanol,
(e) separating the second aqueous phase from the second organic phase,
(f) feeding at least a portion of said separated second aqueous phase to said neutralising (a).

Such a process is for example described in EP-A-4105. In the process as described in EP-A-4105 a mixture obtained by oxidation of cyclohexane and comprising cyclohexylhydroperoxide, acids and carbon dioxide is subjected to a neutralization to neutralize the acids and carbon dioxide present in such oxidation mixture by addition of an aqueous base solution, resulting in a mixture comprising an aqueous phase and an organic phase. After the neutralization, the aqueous phase is separated off and the resulting organic solution is subjected to a decomposition to decompose cyclohexylhydroperoxide into cyclohexanone and cyclohexanol. EP-A-4105 describes that, after completion of the decomposition reaction, the resulting aqueous layer can be separated off and cyclohexanone and cyclohexanol can be isolated from the resultant organic solution by means of distillation.

It has been found that separating aqueous phase from the mixture, obtained after completion of the decomposition reaction, is difficult to carry out. It has also surprisingly been found that the process as described in EP-A-4105 may result in fouling and/or byproduct formation in distillation column(s) in which organic solution obtained in the decomposition is distilled. It has been found that this is caused by slow or incomplete separation of the aqueous phase from the mixture obtained after completion of the decomposition reaction.

Accordingly, it is a goal of the invention to improve the separation of the mixture obtained after decomposition.

This object is achieved by feeding such a portion of the first aqueous phase to said decomposing that the pH of the first aqueous phase is higher than 8.5, measured at 25° C.

It has surprisingly been found that the pH of the first aqueous phase significantly influences the efficiency of the separating of the second aqueous phase from the second organic phase. However, controlling the pH of the first aqueous phase without influencing the pH of the decomposition is difficult to carry out. This is because the pH of the first aqueous phase is largely determined by the pH of the decomposition on the one hand and on the other hand by the acid and/or carbon dioxide concentration in the organic solution fed to the neutralising. For example, controlling the pH of the first aqueous phase can be effected by means of feeding alkali to the neutralising. However, feeding alkali to the neutralising is disadvantageous because it may result in an increased base consumption and/or in a pH of the second aqueous phase different than the desired pH. It has now surprisingly been found that by feeding a portion of the first aqueous phase to said decomposing, the pH of the first aqueous phase can easily be controlled.

Accordingly, the present invention provides a process for preparing cyclohexanone and cyclohexanol, said process comprising
(a) neutralising acids and/or carbon dioxide present in an organic solution further comprising cyclohexylhydroperoxide by mixing the organic solution with a first aqueous base solution to form a first mixture comprising a first aqueous phase and a first organic phase,
(b) separating first aqueous phase from first organic phase,
(c) discharging first aqueous phase,
(d) decomposing cyclohexylhydroperoxide present in said first organic phase by mixing said first organic phase with a second aqueous base solution to form a second mixture comprising a second aqueous phase and a second organic phase comprising cyclohexanone and cyclohexanol,
(e) separating the second aqueous phase from the second organic phase,
(f) feeding at least a portion of said separated second aqueous phase to said neutralising (a), wherein the process further comprises feeding such a portion of the first aqueous phase to said decomposing that the pH of the first aqueous phase is higher than 8.5, measured at 25° C.

It has been found that a pH of the first aqueous phase higher than 8.5 (measured at 25° C.), results in an significant improvement of the separating of the aqueous phase from the mixture obtained after completion of the decomposition reaction, resulting in decreased sodium content in the second organic phase. It has been found that a reduced sodium content in the second organic phase results in less fouling, for example due to salt entrainment, and/or byproduct formation, for example due to aldol condensation, in distillation column(s) in which remaining mixture comprising second organic phase is distilled.

The process of the invention comprises feeding such a portion of the first aqueous phase to the decomposing that the pH of the first aqueous phase has the desired value, i.e. a pH higher than 8.5, measured at 25° C. Preferably, the process of the invention comprises feeding such a portion of the first aqueous phase to the decomposing that the pH of the first aqueous phase is preferably lower than 13, more preferably lower than 11, even more preferably lower than 10.5 and most preferably, from 9 to 10, measured at 25° C. In a preferred embodiment, the pH of the first aqueous phase is controlled by the amount of the separated second aqueous phase fed to the neutralising. Preferably, the amount of the separated second aqueous phase fed to the neutralising is such that the pH of the first aqueous phase is higher than 8.5, measured at 25° C. Preferably, the amount of the separated second aqueous phase fed to the neutralising is such that the pH of the first aqueous phase is lower than 13, measured at 25° C. More preferably, the amount of the separated second aqueous phase fed to the neutralising is such that the pH of the first aqueous phase is from 9 to 10, measured at 25° C.

In the process of the present invention, a portion of the first aqueous phase is fed to the decomposition. In one embodiment, the process of the invention comprises separating first aqueous phase from first organic phase and feeding separated first organic phase and a portion of the separated first aqueous phase to the decomposing. In another embodiment, the process of the invention comprises separating first aqueous phase from first organic phase, mixing separated first organic phase with a portion of the separated first aqueous phase resulting in a second mixture and feeding said second mixture to the decomposing. In still another embodiment, the process of the invention comprises separating a portion of the first aqueous phase from the first mixture resulting in a separated first aqueous phase and in a remaining mixture comprising first organic phase and the other portion of the first aqueous phase and feeding the remaining mixture to the decomposing.

Preferably, said neutralising is carried out at a temperature from 50 to 170° C. More preferably, said neutralising is carried out at a temperature from 50 to 100° C., even more preferably from 50 to 80° C. and even more preferably from 55 to 70° C.

The first mixture obtained in said neutralizing comprises a first aqueous phase comprising neutralized acids and a first organic phase comprising cyclohexylhydroperoxide. The process of the invention further comprises separating first aqueous phase from first organic phase. Said separating may be effected by any suitable method, for example by decantation making use of one or more gravity settlers.

The process of the invention further comprises discharging a portion of the first aqueous phase (the purge). In one embodiment, the process of the invention comprises separating first aqueous phase from first organic phase, discharging a portion of the separated first aqueous phase, feeding separated first organic phase and the other portion of the separated aqueous phase to the decomposing. In another embodiment, the process of the invention comprises separating first aqueous phase from first organic phase, discharging a portion of the separated first aqueous phase, mixing separated first organic phase with the other portion of the separated first aqueous phase resulting in a second mixture and feeding said second mixture to the decomposing. In still another embodiment, the process of the invention comprises separating a portion of the first aqueous phase from the first mixture resulting in a separated first aqueous phase and in a remaining mixture comprising first organic phase and the other portion of the first aqueous phase, discharging the separated first aqueous phase and feeding the remaining mixture to the decomposing.

Said decomposing is preferably effected at a temperature of between 60 to 170° C., more preferably from 60 to 120° C. and even more preferably from 60 to 110° C.

Separating the second aqueous phase from the second organic phase is preferably carried out at a temperature higher than 80° C., more preferably at a temperature higher than 85° C. and even more preferably at a temperature higher than 90° C. Separating the second aqueous phase from the second organic phase at increased temperature results in an increase of the efficiency of the separating. Preferably, separating the second aqueous phase from the second organic phase is carried out at the outlet temperature of the last decomposition reactor. The second mixture obtained in said decomposing comprises a second aqueous phase and a second organic phase comprising cyclohexanone and cyclohexanol. The process of the invention further comprises separating the second aqueous phase from the second organic phase. Preferably, said separating is carried out such that after said separating the sodium content in the second organic phase is less than 100 ppm, more preferably less than 50 ppm and even more preferably less than 10 ppm (relative to the second organic phase). It has surprisingly been found that the pH of the first aqueous phase has a significant effect on the separating of the second aqueous phase from the mixture obtained after completion of the decomposition reaction. Said separating may be effected by any operation known to one skilled in the art for separating aqueous phase from organic phase, for example decantation and/or making use of plate separators or electrostatic separators. In a preferred embodiment, said separating is effected using one or more gravity settlers followed by a plate separator.

In the process of the invention, neutralising acids and/or carbon dioxide present in an organic solution further comprising cyclohexylhydroperoxide is effected by mixing the organic solution with a first aqueous base solution. Said mixing may be effected by any suitable method, for example by using a packed column, a flow or line mixer, a pump, a static mixer, an agitated vessel or combinations thereof. Mixing may also involve injecting the first aqueous base solution into the organic solution.

In the process of the invention, decomposing cyclohexylhydroperoxide present in said first organic phase is effected by mixing said first organic phase with the second aqueous base solution to form a second mixture comprising a second aqueous phase and a second organic phase comprising cyclohexanone and cyclohexanol. Said mixing may be effected by any suitable method, for example by using a packed column, a flow or line mixer, a pump, a static mixer, an agitated vessel or combinations thereof. Mixing may also involve injecting the second aqueous base solution into the remaining mixture. In a preferred embodiment, decomposing is effected in a reaction zone with plug flow characteristics, for example an in-line mixer or several continuous stirred-tank reactors in series.

Preferably, said decomposing is effected in the presence of a water soluble metal salt catalyst that catalyses decomposition of cyclohexylhydroperoxide into cyclohexanone and cyclohexanol, for instance salts of transition metals, such as cobalt, chromium, nickel, iron, manganese and copper. Preference is given to effecting the decomposing with, as transition metal salt, a salt of cobalt and/or of chromium, for instance a sulphate or nitrate. The concentration of the water-soluble metal salt may differ within wide ranges, for instance a concentration of from 0.1 to 100 ppm (calculated as metal and relative to the weight of the aqueous phase). Preferably, a concentration of from 1 to 10 ppm is applied.

The first and second aqueous base solutions refer to aqueous solutions comprising dissolved base(s). Preferably, the base is an earth alkali metal hydroxide and/or one or more salts of an earth alkali metal or the base is an alkali metal hydroxide and/or one or more salts of an alkali metal. Hence, the first and second aqueous base solutions are preferably aqueous solutions comprising an earth alkali metal hydroxide and/or one or more salts of an earth alkali metal or the aqueous base solutions are aqueous solutions comprising an alkali metal hydroxide and/or one or more salts of an alkali metal. More preferably, the first and second aqueous base solutions are aqueous solutions comprising an alkali metal hydroxide and/or one or more salts of an alkali metal. Suitable (earth) alkali metal salts are (earth) alkali metal phosphates, (earth) alkali metal carbonates and (earth) alkali metal bicarbonates. Preferred (earth) alkali metal salts are (earth) alkali metal carbonates and (earth) alkali metal bicarbonates. A preferred earth alkali metal is magnesium. The alkali metal is preferably potassium or sodium, more preferably sodium.

Preferably, the first aqueous base solution is an aqueous solution comprising an alkali metal carbonate, an alkali metal bicarbonate and alkali metal salts of carboxylic acids. More preferably, the first aqueous base solution is an aqueous solution comprising sodium carbonate, sodium bicarbonate and sodium salts of carboxylic acids. Preferably, the sum amount of acid salts, bicarbonate and carbonate of the first aqueous phase is lower than or equal to 40 wt. % and higher than or equal to 20 wt. % (relative to the first aqueous phase).

Preferably, the second aqueous base solution is an aqueous solution comprising an alkali metal hydroxide, preferably sodium hydroxide. More preferably, the second aqueous base solution is an aqueous solution comprising an alkali metal hydroxide, an alkali metal carbonate and alkali metal salts of carboxylic acids. Preferably, the sum amount of acid salts and carbonate of the second aqueous phase is lower than or equal to 40 wt. % and higher than or equal to 20 wt. % (relative to the second aqueous phase).

Preferably, the pH of the second aqueous phase is higher than 13, measured at 25° C. in order to obtain efficient decomposition of cyclohexylhydroperoxide.

The volume ratio of the second aqueous phase to the second organic phase is preferably higher than 0.01, more preferably higher than 0.02, more preferably higher than 0.05 and even more preferably higher than 0.1. Increasing the volume ratio of the second aqueous phase to the second organic phase results in increased decomposition reaction velocity. There is no specific upper limit for the volume ratio of the second aqueous phase to the second organic phase. A volume ratio of the second aqueous phase to the second organic phase higher than 1 may be used, but offer no particular advantage. Therefore, the volume ratio of the second aqueous phase to the second organic phase is preferably lower than 1, more preferably lower than 0.6. In a preferred embodiment, second organic phase is mixed with such a quantity of second aqueous base solution that the volume ratio of the second aqueous phase to the second organic phase has the desired value.

The process of the invention comprises feeding at least a portion of said separated second aqueous phase to said neutralising (a). In a preferred embodiment, the process further comprises feeding a portion of said separated second aqueous phase to said decomposing (d). In a more preferred embodiment, the process comprises, after said separating of the second aqueous phase from the second organic phase, dividing said separated second aqueous phase into two parts, feeding one part (part A) of said separated second aqueous phase to the neutralisation and feeding the other part (part B) of said separated second aqueous phase to the decomposition. Preferably, the first aqueous base solution is part A of said separated second aqueous phase; and a part of the second aqueous base solution is part B of said separated second aqueous phase and the other part of the second aqueous base solution being an aqueous solution of an alkali metal hydroxide. In a preferred embodiment, the second aqueous base solution being a mixture of an aqueous solution of an alkali metal hydroxide and part B of said separated second aqueous phase. Preferably, the amount of aqueous solution of an alkali metal hydroxide fed to the decomposing is such that the pH of the second aqueous phase of the last decomposition reactor has the desired value. Preferably, the pH of the second aqueous phase is higher than 13, measured at 25° C. The process of the invention comprises discharging a portion of the first aqueous phase (the purge). Preferably such a quantity of the first aqueous phase is discharged that accumulation of water in the process of the invention is avoided. In said preferred embodiment, the process of the invention comprises feeding the remaining first aqueous phase to the decomposing. Preferably the amount of the first aqueous phase fed to the decomposing is such that the pH of the first aqueous phase is higher than 8.5 and lower than 13, more preferably higher than 9 and lower than 11 and even more preferably from 9 to 10, measured at 25° C. In said preferred embodiment, the amount of the separated second aqueous phase fed to the neutralisation is such that the pH of the first aqueous phase has the desired value and at the same time accumulation of water in the process is avoided. In said preferred embodiment, the amount of the separated second aqueous phase fed to the decomposing is preferably such that the volume ratio of the second aqueous phase to the second organic phase has the desired value. The volume ratio of the second aqueous phase to the second organic phase is preferably higher than 0.01 and preferably lower than 1. It has surprisingly been found that in this preferred embodiment, feeding a portion of the first aqueous phase to the decomposing results in that the neutralizing and the decomposing can easily be operated at the desired pH resulting in an effective separation of the mixture obtained after the decomposing and at the same time in a high selectivity of the decomposing into cyclohexanone and cyclohexanol and in a decreased base consumption.

The acids and/or carbon dioxide to be neutralized and the cyclohexylhydroperoxide to be decomposed according to the invention may be present in any organic solution comprising acids and cyclohexylhydroperoxide. For example, the organic solution comprising between 0.1 and 20 wt. % cyclohexylhydroperoxide and between 0.1 and 3 wt. % acids (relative to the organic solution).

The cyclohexylhydroperoxide and the acids and/or carbon dioxide which are present in the organic solution fed to said neutralizing can be obtained with various known processes.

Preparing the cyclohexylhydroperoxide and the acids, for example, involves oxidizing cyclohexane with an oxygen containing gas in the presence or absence of substances promoting the decomposition of the cyclohexylhydroperoxide formed resulting in an oxidation mixture comprising cyclohexane, cyclohexanone, cyclohexanol, cyclohexylhydroperoxide, acids, carbon dioxide, esters, low boiling compounds, and high boiling compounds. With low boiling compounds is meant organic compounds having a boiling point lower than cyclohexanone and higher than cyclohexane. Examples are butanol, pentanal, hexanal, pentanol and epoxy-cyclohexane. With high boiling compounds is meant organic compounds having a boiling point higher than cyclohexanol. Examples are 2-cyclohexylidene cyclohexanone, 2-hexylidene cyclohexanone and 2-(cyclohexen-1-yl)cyclohexanone. The oxidation usually takes place in the liquid phase. As oxygen-containing gas use can be made for instance of pure oxygen, air, rich or poor in oxygen, or oxygen mixed with nitrogen or another inert gas. Suitable oxidation temperatures are between 120 and 200° C. Preferably, an oxidation temperature between 140 and 190° C. is used. The oxidation reaction is usually carried out for 5 minutes to 24 hours. The pressure is usually between 0.3 and 5 MPa, preferably between 0.4 and 2.5 MPa.

Preferably, the cyclohexylhydroperoxide to be decomposed according to the invention is obtained by oxidation of cyclohexane with an oxygen-containing gas in the absence of substances promoting the decomposition of the cyclohexylhydroperoxide formed, such as compounds of transition metals, hereinafter referred to as uncatalysed cyclohexane oxidation. Uncatalysed cyclohexane oxidation is preferred to catalysed cyclohexane oxidation because uncatalysed cyclohexane oxidation results in higher yields of cyclohexylhydroperoxide. As a rule, the mixture obtained in such uncatalysed cyclohexane oxidation comprises a weight percentage of cyclohexylhydroperoxide that is at least comparable to the weight percentages of cyclohexanone and cyclohexanol. Often, the amount of cyclohexylhydroperoxide in the reaction mixture obtained in such uncatalysed cyclohexane oxidation is at least two times as large as the amount of cyclohexanone and cyclohexanol. In contrast to the uncatalysed cyclohexane oxidation, the catalysed oxidation—where cobalt and/or chromium compounds are usually applied—cyclohexanol and cyclohexanone are the main products formed, besides a relatively small amount of cyclohexylhydroperoxide, a large portion of the cyclohexylhydroperoxide being already decomposed to cyclohexanol during the oxidation. The catalysed oxidation yields a mixture that contains less than 50% cyclohexylhydroperoxide relative to the weight percentage of cyclohexanol+cyclohexanone. This is often even less than 40% peroxide compared with the weight percentage of cyclohexanol+cyclohexanone. Notwithstanding this, the process according to the invention may also advantageous be applied for decomposing cyclohexylhydroperoxide obtained by catalysed oxidation.

Optionally, prior to subjecting the acids and/or carbon dioxide, present in a mixture obtained by oxidation of cyclohexane with an oxygen-containing gas, to said neutralizing, the mixture obtained by oxidation of cyclohexane with an oxygen-containing gas can be concentrated by separating, preferably by flashing or distilling, all or preferably part of the cyclohexane.

Preferably, the process further comprises, prior to said neutralizing, degassing of entrained and/or dissolved gasses present in the organic solution.

In case the organic solution comprising acids and/or carbon dioxide and cyclohexylhydroperoxide originates from cyclohexane oxidation, the organic solution usually also comprises other compounds, for example (1) cyclohexane and/or (2) cyclohexanone and/or (3) cyclohexanol. The cyclohexylhydroperoxide concentration and the acids concentration in the organic solution is not critical. The cyclohexylhydroperoxide and acids may for example be present in an organic solution comprising between 0.1 and 20 wt. % cyclohexylhydroperoxide and between 0.1 and 3 wt. % (relative to the organic solution). The sum concentration of cyclohexanone and cyclohexanol in the organic solution is not critical and is for instance between 0 and 20 wt. % (relative to the total organic solution).

The process of the invention preferably further comprises distilling the second organic phase, if so desired after washing with water, to obtain cyclohexanone and cyclohexanol.

In a preferred embodiment, the present invention provides a process for the preparation of cyclohexanone and cyclohexanol, said process comprising
(1) Oxidizing cyclohexane with an oxygen-containing gas to obtain an organic solution comprising cyclohexylhydroperoxide, cyclohexane, cyclohexanol, cyclohexanone, acids, carbon dioxide, esters, low boiling compounds and high boiling compounds;
(2) Optionally, separating part of the cyclohexane from said organic solution;
(3) Neutralizing acids and carbon dioxide formed in the oxidation by mixing the organic solution with a first aqueous base solution to form a first mixture comprising a first aqueous phase and a first organic phase;
(4) Separating first aqueous phase from first organic phase;
(5) Discharging first aqueous phase;
(6) Decomposing cyclohexylhydroperoxide present in said first organic phase by mixing said first organic phase with a second aqueous base solution to form a second mixture comprising a second aqueous phase and a second organic phase comprising cyclohexanone and cyclohexanol,
(7) Separating the second aqueous phase from the second organic phase;
(8) Distilling the second organic phase to obtain cyclohexanone and cyclohexanol.

In this preferred embodiment, distilling the second organic phase to obtain cyclohexanone and cyclohexanol preferably comprises the following steps: separating cyclohexane from the second organic phase (7.a), separating low boiling compounds from the second organic phase (7.b), separating cyclohexanone from the second organic phase (7.c) and separating cyclohexanol from the second organic phase (7.d). Other purification and/or recovery steps may be carried out between (7.a), (7.b), (7.c) and/or (7.d).

More preferably, in this preferred embodiment, distilling the second organic phase to obtain cyclohexanone and cyclohexanol comprises separating, by distillation, cyclohexane from the second organic phase to obtain a top product comprising cyclohexane and a first bottom product comprising cyclohexanone, cyclohexanol, low boiling compounds and high boiling compounds; separating, by distillation, low boiling compounds from the first bottom product to obtain a top product comprising low boiling compounds and a second bottom product comprising cyclohexanone, cyclohexanol and high boiling compounds; and separating, by distillation, cyclohexanone from the second bottom product to obtain a top product comprising cyclohexanone and a third bottom product comprising cyclohexanol and high boiling compounds; and separating, by distillation, cyclohexanol from the third bottom product to obtain a top product comprising cyclohexanol and a bottom product comprising high boiling compounds. Cyclohexanol may subsequently be subjected to a dehydrogenation reaction. Other purification and/or recovery steps may be carried out between the above mentioned distillation steps.

DESCRIPTION OF AN EMBODIMENT

Figure 1:
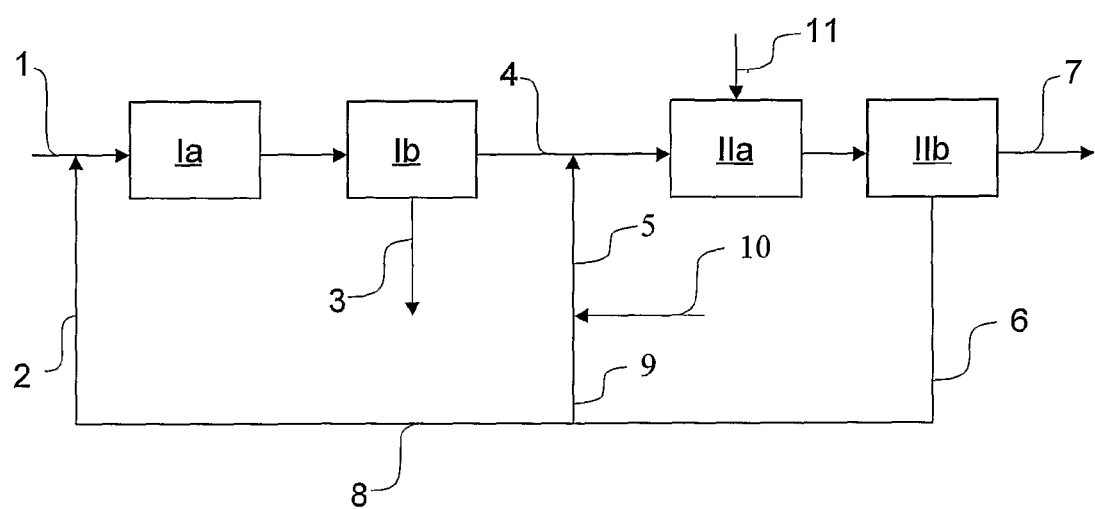
FIG. 1 represents a preferred embodiment of the process according to the invention. In this figure, the symbols have the following meaning:
(1)=organic solution
(2)=first aqueous base solution
(3)=first aqueous phase
(4)=first organic phase and first aqueous phase
(5)=second aqueous base solution
(6)=second aqueous phase
(7)=second organic phase
(8)=part A
(9)=part B
(10)=aqueous solution of an alkali metal hydroxide
(11)=aqueous solution of a water-soluble transition metal salt catalyst
Ia=neutralisation reactor(s)
Ib=liquid/liquid separator(s)
IIa=decomposition reactor(s)
IIb=liquid/liquid separator(s)

Referring to FIG. 1, Ia represents a neutralisation reactor. Line 1 represents an organic solution comprising acids, carbon dixode and cyclohexyllhydroperoxide. Line 2 represents a first aqueous base solution, which is a part (part A) of the second aqueous phase (line 6) obtained in the separator (the last separator in case the separating of the mixture obtained in the decomposition involves more than one separator). The organic solution is pre-mixed with the first aqueous base solution before being fed to neutralisation reactor Ia. After neutralising the first mixture comprising a first aqueous phase and a first organic phase is supplied to liquid/liquid separator Ib, where first aqueous phase and first organic phase are separated. A portion of the separated first aqueous phase is discharged through line 3. The remaining mixture (line 4) comprising first organic phase and the other portion of the first aqueous phase is pre-mixed with the second aqueous base solution (line 5) before being fed to decomposition reactor IIa (the first decomposition reactor in case the decomposing is effected in a series of decomposition reactors). The second aqueous base solution is obtained by mixing a part (part B) (line 9) of the second aqueous phase (line 6) obtained in the separator (the last separator in case the separating of the mixture obtained in the decomposition involves more than one separator) with an aqueous solution of an alkali metal hydroxide (line 10), preferably sodium hydroxide. An aqueous solution of a water-soluble transition metal salt catalyst is fed to decomposition reactor IIa through line 11. In case the decomposing is effected in a series of decomposition reactors, the above-mentioned streams are fed to the first decomposition reactor. After decomposing, the second mixture comprising the second aqueous phase and the second organic phase is supplied to liquid/liquid separator IIb (the first separator in case the separating of the mixture obtained in the decomposition involves more than one separator), where the second aqueous phase (line 6) is separated from the second organic phase (line 7). The second organic phase (line 7) is distilled, optionally after washing with water, to obtain cyclohexanone and cyclohexanol.

The invention will be elucidated by the following examples without being limited thereto.

EXAMPLE 1

An oxidation mixture (line 1 in FIG. 1), obtained from an uncatalyzed cyclohexane oxidation, consisted of cyclohexane, 3.2 wt. % cyclohexylhydroperoxide, 0.5 wt. % cyclohexanol, 0.3 wt. % cyclohexanone and by-products. Among other by-products, this mixture also contained 0.02 wt. % $CO_2$ and 0.4 wt. % mixed organic acids (mono and di-acids ranging from C1 to C6). The oxidation mixture was cooled to 60° C. Before being fed to a well-stirred neutralization reactor (Ia in FIG. 1), the cooled oxidation mixture was pre-mixed with an aqueous base solution (line 2 in FIG. 1) obtained from the plate separator after the cyclohexylhydroperoxide decomposition reactors. The aqueous base solution (line 2) contained 4.1 wt % $Na_2CO_3$, 1.4 wt % NaOH and 14.6 wt. % sodium-carboxylates of mixed monoacids and di-acids ranging from C1 to C6 acids. Both aqueous and organic solutions were thoroughly mixed in the neutralization reactor (Ia) to obtain a fine organic-aqueous emulsion. The aqueous phase content in this emulsion was 3.8 vol. %. At the outlet of this reactor, $CO_2$ and organic acids were quantitatively neutralized. The temperature at the outlet of the neutralisation reactor was 65° C. After this reactor, the emulsion was supplied to a gravity settler (Ib in FIG. 1) in which aqueous phase is separated from the emulsion. The resulting aqueous phase contained 0.3 wt. % $Na_2CO_3$, 3.6 wt. % $NaHCO_3$ and 21.5 wt. % Na-carboxylates of mixed monoacids and di-acids ranging from C1 to C6 acids (No NaOH). The amount of stream 2 was chosen such that the pH of the aqueous phase leaving the gravity settler was 9.1. Since the total surplus of aqueous phase in neutralization and decomposition steps is completely purged at this point in the process (purge stream 3), this pH could only be obtained by adjusting the purge stream in a way that 35% of this stream was sent, together with the separated organic phase, to the first decomposition reactor (stream 4). Thus the amount of the aqueous phase purged (line 3 in FIG. 1) was 65% of the aqueous phase leaving the gravity-settler. Thus, 35% of the aqueous phase leaving the gravity settler was united with the separated organic phase (line 4 in FIG. 1). The resulting mixture (line 4) was pre-mixed with an aqueous base solution (line 5) before being fed to the first well-stirred decomposition reactor IIa. The aqueous base solution (line 5) was obtained by mixing a part (line 9) of the aqueous base solution (line 6 in FIG. 1) obtained from the plate separator after the cyclohexylhydroperoxide decomposition reactors with an aqueous NaOH solution (line 10). An additional aqueous NaOH solution (line 10) was fed to stream 9 to replenish the consumed base in the neutralization and decomposition process. The amount of NaOH fed was such that the NaOH concentration in the aqueous phase at the outlet of the last decomposition reactor was 0.4 mol/liter. Also a small amount of aqueous solution of cobalt sulphate (line 11 in FIG. 1) was added to the first decomposition reactor as catalyst for the decomposition of cyclohexylhydroperoxide to cyclohexanol and cyclohexanone. The concentration of cobalt in the aqueous phase present in the decomposition reactors was approx. 5 ppm. After the last decomposition reactor the cyclohexylhydroperoxide conversion was complete. Due to the adiabatic temperature rise the temperature at the outlet of the last decomposition reactor was 95° C. The obtained emulsion at the outlet of this reactor was allowed to settle (IIb in FIG. 1) in 2 consecutive gravity-settlers followed by a plate-separator. After L/L separation the sodium content of the resulting organic phase (line 7 in FIG. 1) was less than 5 ppm, demonstrating an effective removal of the aqueous phase. The separated organic phase comprised mainly cyclohexane and further 1.7 wt. % cyclohexanone and 1.7 wt. % cyclohexanol. This corresponded to a selectivity of the cyclohexylhydroperoxide decomposition reaction of 91.5%. The aqueous phase from the L/L separators after the decomposition reactors was largely recycled to the first decomposition reactor (line 9 in FIG. 1). The size of this stream was controlled such that the decomposition reactors contained approx. 15 vol. % of aqueous phase. A minor part of the aqueous phase from the L/L separators after the decomposition reactors was fed to the feed of the neutralization reactor (line 8 of FIG. 1). In this experiment the total NaOH consumption was 96 kg per ton of produced cyclohexanone+cyclohexanol.

Comparative Experiment

Example 1 was repeated, with the exception that the amount of stream 2 was chosen such that the separated aqueous phase leaving the gravity settler Ib was completely purged (stream 3). Thus, the separated aqueous phase leaving the gravity settler Ib was not fed to the decomposition IIa. In this experiment the separation of the aqueous and organic phases became very difficult and unfavorable effects occurred in downstream operations (fouling and yield-loss in reboilers).

The invention claimed is:

1. Process for preparing cyclohexanone and cyclohexanol which comprises:
   (a) subjecting an organic solution which comprises acids, carbon dioxide and cyclohexylhydroperoxide to a neutralisation step so as to neutralise the acids and/or carbon dioxide therein by mixing the organic solution with a first aqueous base solution in the absence of an added alkali feed to form a first mixture comprising a first aqueous phase and a first organic phase,
   (b) separating the first aqueous phase from the first organic phase,
   (c) discharging the first aqueous phase,
   (d) decomposing cyclohexylhydroperoxide present in the first organic phase by mixing the first organic phase with a second aqueous base solution to form a second mixture comprising a second aqueous phase and a second organic phase comprising cyclohexanone and cyclohexanol,
   (e) separating the second aqueous phase from the second organic phase, (f) feeding at least a portion of the separated second aqueous phase to the neutralising step (a), wherein
the neutralising step (a) comprises feeding a portion of the first aqueous phase to the decomposing step (d) in an amount that controls the pH of the first aqueous phase to higher than 8.5 as measured at 25° C.

2. Process according to claim 1, wherein the portion of the first aqueous phase fed to the decomposing step (d) is in an amount that controls the pH of the first aqueous phase to lower than 13 as measured at 25 C.

3. Process according to claim 1, wherein the portion of the first aqueous phase fed to the decomposing step (d) is in an amount that controls the pH of the first aqueous phase to from 9 to 10 as measured at 25° C.

4. Process according to claim 1, wherein the separated second aqueous phase is fed to the neutralising step (a) in an amount such that the pH of the first aqueous phase is higher than 8.5 as measured at 25° C.

5. Process according to claim 2, wherein the separated second aqueous phase is fed to the neutralising step (a) in an amount such that the pH of the first aqueous phase is lower than 13 as measured at 25° C.

6. Process according to claim 3, wherein the separated second aqueous phase is fed to the neutralising step (a) in an amount such that the pH of the first aqueous phase is from 9 to 10 as measured at 25° C.

7. Process according to claim 1, wherein the pH of the second aqueous phase is higher than 13 as measured at 25° C.

8. Process according to claim 1, which comprises feeding a portion of the separated second aqueous phase to the decomposing step (d).

9. Process according to claim 1, which further comprises dividing the separated second aqueous phase into two parts, feeding one part (part A) of the separated second aqueous phase to the neutralising step (a) and feeding the another part (part B) of said separated second aqueous phase to the decomposing step (d).

10. Process according to claim 9, wherein the first aqueous base solution is part A of the separated second aqueous phase, a part of the second aqueous base solution is part B of the separated second aqueous phase and another part of the second aqueous base solution is an aqueous solution of an alkali metal hydroxide.

11. Process according to claim 10, wherein the aqueous solution of an alkali metal hydroxide is in an amount such that the pH of the second aqueous phase is higher than 13 as measured at 25° C.

12. Process according to claim 9, wherein the separated second aqueous phase is fed to the decomposing step (d) in an amount such that the volume ratio of the second aqueous phase to the organic phase is higher than 0.01 and lower than 1.

13. Process according to claim 1, which further comprises distilling the second organic phase to obtain cyclohexanone and cyclohexanol.

* * * * *